(12) United States Patent
Moehle et al.

(10) Patent No.: US 8,100,863 B2
(45) Date of Patent: Jan. 24, 2012

(54) CATHETER ASSEMBLY, CATHETER SYSTEMS INCLUDING SAME, AND METHOD OF MANUFACTURE

(75) Inventors: Ryan T. Moehle, Salt Lake City, UT (US); Charles L. Farnworth, Riverton, UT (US); Dwight Hibdon, Park City, UT (US); Ryan C. Patterson, Kaysville, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 699 days.

(21) Appl. No.: 11/368,953

(22) Filed: Mar. 6, 2006

(65) Prior Publication Data

US 2006/0200111 A1   Sep. 7, 2006

Related U.S. Application Data

(60) Provisional application No. 60/658,556, filed on Mar. 4, 2005.

(51) Int. Cl.
*A61M 5/32* (2006.01)

(52) U.S. Cl. ........................................ 604/175
(58) Field of Classification Search .................. 604/174, 604/175
See application file for complete search history.

(56) References Cited

U.S. PATENT DOCUMENTS

| | | | |
|---|---|---|---|
| 4,278,092 A * | 7/1981 | Borsanyi et al. | 604/175 |
| 4,507,353 A * | 3/1985 | Kuhlmann et al. | 428/222 |
| 4,950,259 A | 8/1990 | Geary et al. | 604/254 |
| 5,053,023 A * | 10/1991 | Martin | 604/523 |
| 5,057,075 A * | 10/1991 | Moncrief et al. | 604/500 |
| 5,156,592 A * | 10/1992 | Martin et al. | 604/43 |
| 5,190,529 A | 3/1993 | McCrory et al. | |
| 5,308,338 A * | 5/1994 | Helfrich | 604/175 |
| 5,509,902 A | 4/1996 | Raulerson | |
| 5,599,311 A | 2/1997 | Raulerson | |
| 5,624,413 A | 4/1997 | Markel et al. | 604/523 |
| 5,830,184 A | 11/1998 | Basta | 604/104 |
| 5,833,664 A | 11/1998 | Seare, Jr. | 604/174 |
| 5,879,342 A * | 3/1999 | Kelley | 600/524 |
| 5,944,732 A | 8/1999 | Raulerson et al. | 606/167 |
| 6,033,382 A | 3/2000 | Basta | 604/104 |
| 6,280,423 B1 | 8/2001 | Davey et al. | 604/264 |

(Continued)

FOREIGN PATENT DOCUMENTS

WO     2007089700 A2     8/2007

*Primary Examiner* — Nicholas Lucchesi
*Assistant Examiner* — Aarti B Berdichevsky
(74) *Attorney, Agent, or Firm* — Rutan & Tucker, LLP (57) ABSTRACT

A catheter assembly is disclosed comprising a catheter, a tubular structure affixed to an exterior surface of the catheter, and a stabilizing cuff affixed to, and at least partially embedded within, the tubular structure. The tubular structure may include a tapered surface extending from an end of the tubular structure to an exterior surface of the catheter. A method of manufacturing a catheter assembly is also disclosed. For example, such a method may comprise positioning a tubular structure about a catheter, positioning a stabilizing cuff near the tubular structure, and partially embedding at least a portion of the stabilizing cuff within the tubular structure while shaping the tubular structure to form a tapered surface. A temporary sleeve may be positioned about the tubular structure prior to shaping the tubular structure. The tubular may also be performed to include a tapered end prior to positioning the tubular structure about the catheter.

14 Claims, 7 Drawing Sheets

U.S. PATENT DOCUMENTS

| | | |
|---|---|---|
| 6,342,120 B1 | 1/2002 | Basta ............................ 156/242 |
| 6,682,519 B1 | 1/2004 | Schon ........................... 604/508 |
| 6,730,096 B2 | 5/2004 | Basta ............................ 606/108 |
| 6,926,721 B2 | 8/2005 | Basta |
| 7,335,184 B2 * | 2/2008 | Laguna .................... 604/101.02 |
| 7,604,617 B2 * | 10/2009 | Porter et al. .................. 604/175 |
| 2002/0032411 A1 | 3/2002 | Basta |
| 2004/0199110 A1 | 10/2004 | Basta |
| 2005/0279354 A1 * | 12/2005 | Deutsch et al. .......... 128/200.24 |
| 2006/0129134 A1 | 6/2006 | Kerr |
| 2006/0135946 A1 * | 6/2006 | Moehle et al. ................. 604/513 |
| 2007/0112334 A1 * | 5/2007 | Porter et al. .................. 604/539 |
| 2007/0149949 A1 * | 6/2007 | Porter et al. .................. 604/523 |
| 2007/0244490 A1 | 10/2007 | Moehle et al. |

* cited by examiner

CATHETER ASSEMBLY, CATHETER SYSTEMS INCLUDING SAME, AND METHOD OF MANUFACTURE

CROSS REFERENCE TO RELATED APPLICATION

This application is entitled to the benefit of U.S. Provisional Application No. 60/658,556, filed Mar. 4, 2005.

BACKGROUND

Over the years, various apparatuses and devices have been developed for the purpose of introducing and removing fluids from bodies, such as the human body. Examples of such devices include catheters, shunts, drainage tubes, and other tubular medical devices as known in the art, broadly referred to hereafter as "catheters." Such catheters may be positioned in various locations within a body and, once in place, may be anchored by a stabilizing device.

One example of a conventional catheter stabilizing device is a tissue-ingrowth cuff. Tissue-ingrowth cuffs are typically made of a biocompatible fabric, such as polyester, and are typically attached to the outer surface of a catheter or cannula by an adhesive. In many conventional catheters, the cuff is positioned on the catheter such that when the distal portion of the catheter is fully inserted into the body, the cuff is located in subcutaneous tissue, such as a subcutaneous tunnel. A subcutaneous tunnel such as this can be formed by a tunneling tool, such as a trocar, either before or after inserting the distal end of the catheter into a bodily cavity, duct, vessel, or the like. The proximal portion of the catheter having the cuff may then be drawn through the tunnel by the tool while the tool passes through the subcutaneous tissue. In many conventional catheters, an adhesive is applied to the cuff fabric to matte the fabric in an attempt to reduce the amount of force needed to tunnel the catheter. The stabilizing cuff is also typically sized such that upon completion of the catheterization procedure, the cuff fits snugly in the tunnel or other area.

Upon completion of the catheterization procedure, surrounding tissue in the body grows into the biocompatible fabric of the cuff to further stabilize the catheter in the catheterized location. In addition to stabilizing the catheter, the ingrown tissue helps to seal off the catheterized location and subcutaneous tunnel from foreign bodies, which may also prevent patient infection. Ingrown tissue may also prevent blood from exiting or pooling around the catheter near the exit site.

Although conventional fabric cuffs are inexpensive to make and are generally effective at stabilizing a catheter, difficulty remains in inserting and removing such cuffs into/from a patient. Specifically, because adhesive is used to affix conventional cuffs to the catheter, the ultimate size and profile of the cuff structure (and catheter assembly) may be adversely increased based on the amount and thickness of the adhesive used, which may vary. The integrity of conventional cuff structures is also at least partially dependent on, and may be weakened by, the adhesive bond formed between the cuff structure and the catheter. In addition, the adhesive used to matte the cuff fabric may impede tissue ingrowth or result in a rigid, inflexible cuff structure.

Accordingly, there is a need for a robust stabilizing device that improves upon the prior art. There is also need for improved methods of manufacturing cuff structures.

SUMMARY

According to at least one embodiment, a catheter assembly may comprise a catheter including an inner surface defining one or more elongated lumens therein, a tubular structure affixed to an exterior surface of the catheter, and a stabilizing cuff affixed to, and at least partially embedded within, the tubular structure. In certain embodiments, the tubular structure includes at least one tapered surface extending from an end of the tubular structure to an exterior surface of the catheter. The stabilizing cuff may also be positioned substantially within an annular recess defined in the tubular structure. The catheter and tubular structure may comprise at least one thermoplastic polyurethane resin. In addition, at least one of the thermoplastic polyurethane resins utilized in the catheter may be identical to a thermoplastic polyurethane resin utilized in the tubular structure.

In at least one embodiment, the exterior surface of the tubular structure may be at least partially conical in shape. In addition, the tubular structure may be configured to initially snugly fit around the catheter shaft (i.e., an inner diameter of the tubular structure may be configured to initially snugly fit around an exterior surface of the catheter shaft). The tapered surface of the tubular structure may also be configured to exhibit a length of between about 1 to about 3 centimeters.

According to at least one exemplary embodiment, a method of forming a catheter assembly may comprise providing a catheter, positioning a tubular structure about the catheter, positioning a stabilizing cuff near the tubular structure, and shaping the tubular structure to form a tapered surface extending from an exterior surface of the catheter. The method may also comprise affixing the stabilizing cuff to the tubular structure and embedding at least a portion of the stabilizing cuff within the tubular structure. In addition, the tubular structure may be shaped by exceeding a transition temperature (e.g., a melting, softening or glass transition temperature) of the tubular structure.

In certain embodiments, the method may comprise radially biasing the stabilizing cuff toward the catheter while exceeding a transition temperature of the tubular structure. The method may also comprise positioning a temporary sleeve about the tubular structure prior to shaping the tubular structure. In addition, the tubular structure may be preformed to include at least one tapered end prior to positioning the tubular structure about the catheter. An adhesion-resistant coating may also be applied to the tubular structure prior to shaping the tubular structure.

Features from any of the above-mentioned embodiments may be used in combination with one another in accordance with the general principles described herein. These and other embodiments, features and advantages will be more fully understood upon reading the following detailed description in conjunction with the accompanying drawings and claims.

BRIEF DESCRIPTION OF THE DRAWINGS

The accompanying drawings illustrate a number of exemplary embodiments and are a part of the specification. Together with the following description, these drawings demonstrate and explain the principles of the instant disclosure.

Throughout the drawings, identical reference characters and descriptions indicate similar, but not necessarily identical, elements. While the exemplary embodiments described herein are susceptible to various modifications and alternative forms, specific embodiments have been shown by way of example in the drawings and will be described in detail herein. However, one of skill in the art will understand that the exemplary embodiments described herein are not intended to be limited to the particular forms disclosed. Rather, the instant disclosure covers all modifications, equivalents, and alternatives falling within the scope defined by the appended claims.

DETAILED DESCRIPTION

Figure 1:
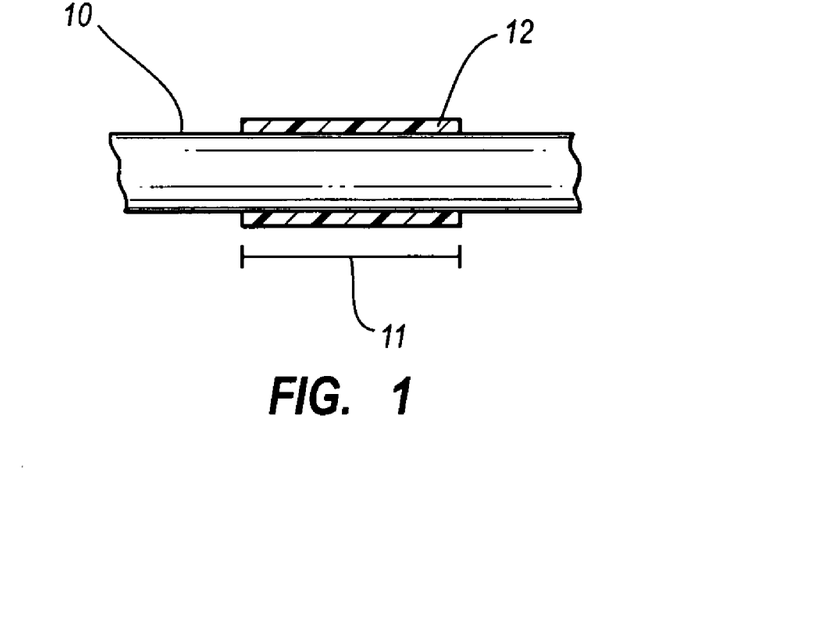
FIGS. 1-3 illustrate an exemplary method of manufacturing a catheter assembly.
Figure 2:
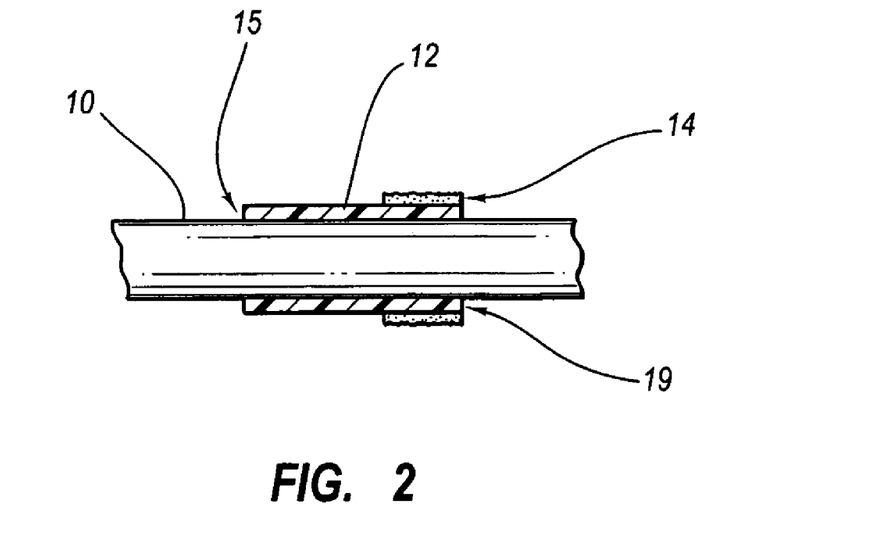
Figure 3:
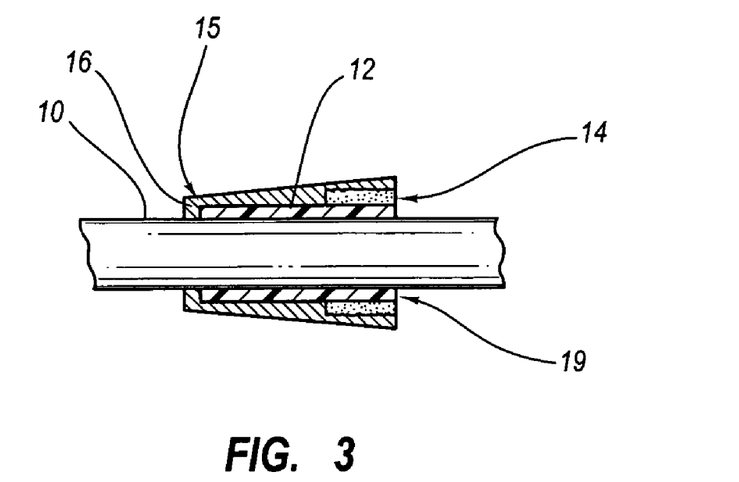
Figure 6:
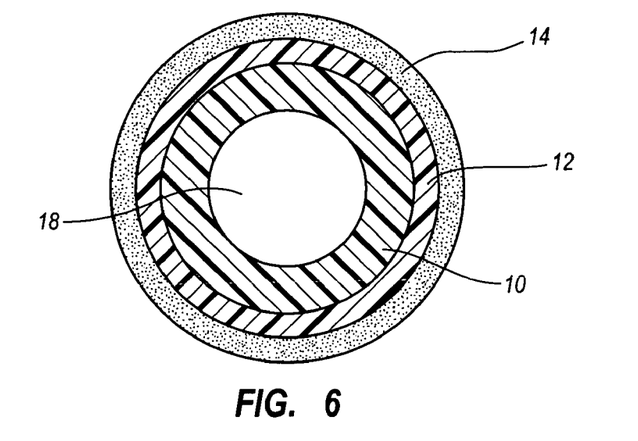
FIG. 6 is a cross-sectional view of the catheter assembly illustrated in FIG. 4, taken along line A-A.

FIGS. 1-3 illustrate, in schematic cross-sectional views, an exemplary method of manufacturing a catheter assembly. As seen in FIG. 1, in at least one embodiment a tubular structure 12 is slid over, or positioned generally about, the exterior surface of a catheter 10. In certain embodiments, catheter 10 defines an elongated lumen 18 (FIG. 6). Catheter 10 generally represents any catheter or cannula capable of introducing or removing fluid from a body, such as a human body. For example, catheter 10 may be a single or multi-lumen catheter, a shunt or drainage tube, or the like intended for permanent, semi-permanent, or temporary placement. Catheter 10 may also comprise any catheter or cannula used in connection with infusion, cardiovascular access, renal treatment, hemodialysis, hemodynamic monitoring, parenteral nutrition, peritoneal dialysis, oncologic treatment, or any other function such as simultaneous aspiration and infusion, without limitation.

Catheter 10 and/or tubular structure 12 may comprise any material exhibiting suitable biocompatibility and/or biostability characteristics. In at least one embodiment, catheter 10 and tubular structure 12 comprise a biocompatible plastic or elastomer, such as a medical-grade thermoplastic polyurethane resin ("TPU"). Examples of suitable TPUs include, without limitation, aliphatic polyether-based polyurethanes, aromatic polyether-based polyurethanes, and aliphatic polycarbonate-based polyurethanes. In certain embodiments, catheter 10 may comprise at least one thermoplastic polyurethane resin that is identical to a thermoplastic polyurethane resin utilized in tubular structure 12.

Tubular structure 12 may be formed in any number of shapes and sizes and may be positioned to at least partially surround catheter 10. In at least one embodiment, tubular structure 12 includes an aliphatic polycarbonate-based polyurethane and is configured to snugly fit around the catheter shaft (i.e., around an exterior surface of the catheter shaft). In certain embodiments, tubular structure 12 may also be configured to exhibit an initial length 11 (FIG. 1) of between about 1 to about 3 centimeters. In addition, as illustrated in FIG. 2, tubular structure 12 may be configured to include a leading end 15 and a trailing end 19, taken with respect to an intended direction of insertion or advancement of catheter 10 within a body.

As seen in FIG. 2, a stabilizing cuff 14 may be positioned near or proximate to tubular structure 12. Depending on the intended direction of insertion or advancement of catheter 10, stabilizing cuff 14 may be positioned near the center of tubular structure 12, near leading end 15, or near trailing end 19 (as is the case in FIG. 2). In certain embodiments, stabilizing cuff 14 comprises a fabric cuff for encouraging tissue ingrowth subsequent to positioning stabilizing cuff 14 within a body. Generally speaking, stabilizing cuff 14 may be formed of any number or combination of materials capable of promoting tissue ingrowth, including, for example, polyesters such as polyethylene terephthalate. Stabilizing cuff 14 may also be formed in any number of shapes or sizes. In at least one embodiment, stabilizing cuff 14 comprises a strip or portion of a substantially planar sheet of tissue ingrowth fabric exhibiting a width equal to about 8 millimeters. In other embodiments, the stabilizing cuff 14 can have varying widths, for example, about 6 or about 10 millimeters.

As seen in FIGS. 3 and 6 (discussed in detail below), stabilizing cuff 14 may be wrapped around (i.e., circumferentially surround) tubular structure 12 to cover the entire outer circumference of tubular structure 12. Further, as discussed in greater detail below in connection with FIG. 7, stabilizing cuff segments 114 may be placed about select portions of an outer circumference of tubular structure 112. After stabilizing cuff 14 has been positioned about tubular structure 12, heat and/or pressure may then be applied to tubular structure 12 and stabilizing cuff 14 to affix stabilizing cuff 14 to tubular structure 12. In certain embodiments, heat and pressure are applied using complementary "cuffing jaws," which comprise heat-conductive molds comprising a selected external shape, as known in the art. According to at least one embodiment, stabilizing cuff 14 is affixed to tubular structure by closing a set of cuffing jaws onto stabilizing cuff 14 and tubular structure 12 at a temperature of about 375-380° Fahrenheit for around 15 to 45 seconds at about 60 psi.

After stabilizing cuff 14 is affixed to tubular structure 12, a temporary sleeve 16 may be positioned about tubular structure 12 and stabilizing cuff 14, as illustrated in FIG. 3. Temporary sleeve 16 may be formed in any number of shapes and sizes. In at least one embodiment, a length of temporary sleeve 16 may be equal to or greater than tubular structure 12. For example, the length of temporary sleeve 16 may be about 0.5 to about 1 inches longer than length 11 (FIG. 1) of tubular structure 12. Temporary sleeve 16 may also be centrally positioned about tubular structure 12, such that the midpoint of temporary sleeve 16 is substantially aligned with the midpoint of tubular structure 12.

In one exemplary embodiment, temporary sleeve 16 comprises a heat-shrinkable material that contracts or shrinks when heat is applied. Although temporary sleeve 16 may be formed in any number of shapes and sizes, in at least one embodiment temporary sleeve 16 may be configured to include a pre-shrunk inner diameter of about 0.300 inches, and a shrunken or contracted inner diameter (i.e., after sufficient heat has been applied to the sleeve 16 to cause it to contract) substantially equivalent to the outer diameter of the catheter body.

In this exemplary embodiment, temporary sleeve 16 may be used both to compress or bias stabilizing cuff 14 and tubular structure 12 and to mold tubular structure 12 into a desired shape. For example, after sliding temporary sleeve 16 over both tubular structure 12 and stabilizing cuff 14, heat may be applied to both temporary sleeve 16 and tubular structure 12 until a transition point (e.g., a melting/softening temperature or glass transition temperature) of one or both materials is reached and/or exceeded. Heat may be applied to tubular structure 12 and/or stabilizing cuff 14 in any number of ways known in the art, including, for example, by applying hot air using a hot air system. In at least one embodiment, air heated to a temperature of about 380° Fahrenheit is applied to tubular structure 12 and stabilizing cuff 14 until tubular structure 12 begins to softens or melts and temporary sleeve 16 begins to shrink or contract. As tubular structure 12 softens or melts, and as temporary sleeve 16 contracts, the contracting pressure applied by temporary sleeve 16 may bias and force tubular structure 12 into a desired shape. In at least one embodiment, this contracting pressure forces the tubular structure 12 into the tapered shape illustrated in FIG. 4. Specifically, the contracting pressure applied by temporary sleeve 16 may create a smooth and tapered transition between the exterior surface of catheter 10 and stabilizing cuff 14. Temporary sleeve 16 may then be removed to allow the heated elements to cool, resulting in an exemplary catheter assembly 30.

In another embodiment, temporary sleeve 16 may comprise a material (e.g., silicone) that does not shrink or contract in response to the application of heat. In this exemplary embodiment, a secondary set of cuffing jaws or molds may be used to compress or mold tubular structure 12 into a desired shape. For example, a secondary set of cuffing jaws embodying the inverse of the desired shape may be closed onto stabilizing cuff 14 and tubular structure 12 at a temperature of about 275° Fahrenheit at about 30 psi for around 45 seconds. Once a transition point (e.g., a melting/softening temperature or glass transition temperature) of tubular structure 12 is reached and/or exceeded, tubular structure 12 will begin to soften, melt, or even liquefy. As tubular structure 12 softens, the pressure applied by the cuffing jaws or mold may bias or force tubular structure 12 into a desired shape. In at least one embodiment, the heat and pressure applied by the cuffing jaws forces the tubular structure 12 into the tapered shape illustrated in FIG. 4, resulting in a smooth and tapered transition between the exterior surface of catheter 10 and stabilizing cuff 14. The cuffing jaws and temporary sleeve 16 may then be removed to allow the heated elements to cool, resulting in exemplary catheter assembly 30.

In the exemplary embodiment previously described (wherein a secondary set of cuffing jaws is used to shape tubular structure 12 into a desired shape, as opposed to using a heat-shrinkable material to shape the structure), temporary sleeve 16 may comprise an adhesion-resistant material, such as, for example, silicone, to inhibit adhesion between the cuffing jaws or mold and tubular structure 12.

Figure 4:
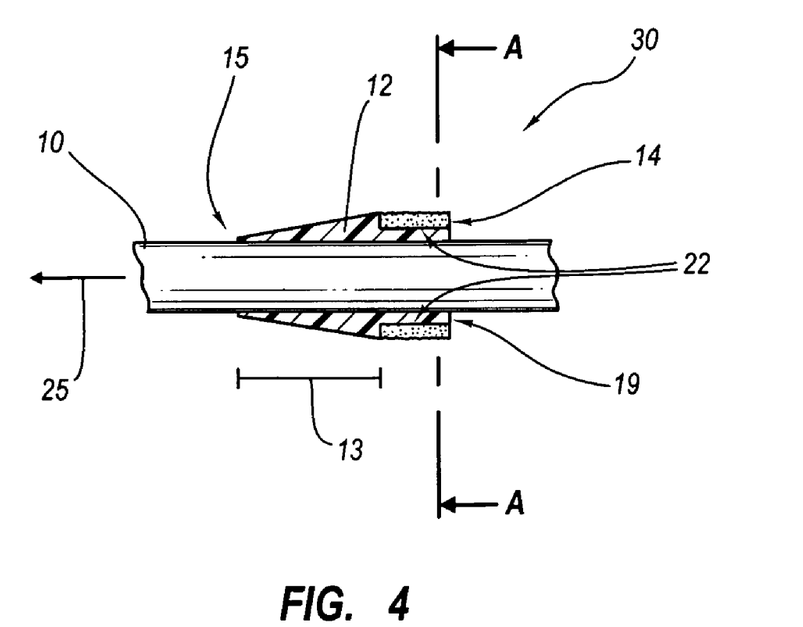
FIG. 4 is a partial schematic cross-sectional view of a catheter assembly according to at least one embodiment.

As illustrated in FIG. 4, in at least one embodiment, a catheter assembly 30 is created (in accordance with one or more of the processes described herein) comprising a tubular structure 12 including a leading end 15 shaped so as to facilitate advancement of stabilizing cuff 14 within a body. In certain embodiments, leading end 15 of tubular structure 12 is forced into the tapered shape illustrated in FIG. 4, resulting in a smooth and tapered transition from the outer diameter of catheter 10 to stabilizing cuff 14. Such a transition may generally extend radially outwardly from the outer diameter of catheter 10 at a leading end 15 of tubular structure 12 in a tapered fashion toward a trailing end 19 of tubular structure 12. In at least one embodiment, such a transition results in tubular structure 12 including an exterior surface that is at least partially conical in shape. Shaping tubular structure 12 in this manner effectively reduces the amount of force required to advance catheter 10 in a tunnel insertion direction 25.

Figure 7:
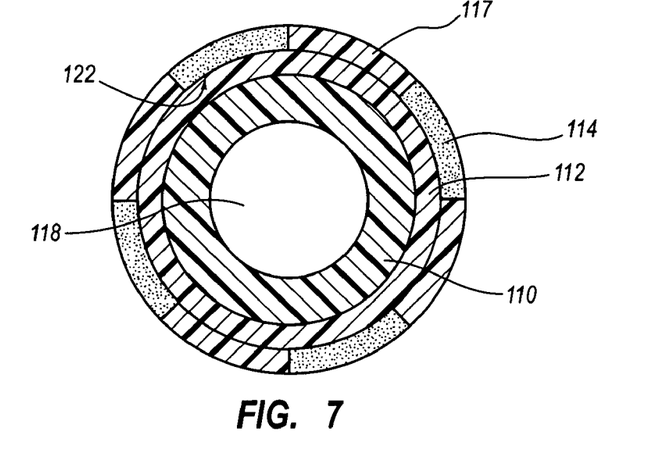
FIG. 7 is a cross-sectional view of an additional embodiment of a catheter assembly.

As shown in FIG. 4, an annular recess 22 may be defined in tubular structure 12. In at least one embodiment, as illustrated in FIG. 4, stabilizing cuff 14 may be positioned substantially within annular recess 22. In certain embodiments, annular recess 22 may be circumferentially continuous about substantially a selected circumference of tubular structure 12. For example, as illustrated in FIG. 6, annular recess 22 may be defined about a selected circumferential region of tubular structure 12, such that, when stabilizing cuff 14 is positioned within annular recess 22, stabilizing cuff 14 extends continuously, circumferentially around tubular structure 12. In another embodiment, one or more circumferentially separated recesses may be defined along select portions of the outer diameter of tubular structure. For example, as illustrated in FIG. 7, a plurality of recesses 122 may be defined along select portions of tubular structure 112. A plurality of stabilizing cuff portions 114 may then be positioned within recesses 112, separated by a plurality of protrusions 117.

In addition to shaping tubular structure 12 in the manner illustrated in FIGS. 1-4, the application of pressure and heat by cuffing jaws and/or temporary sleeve 16 may flatten or smooth the surface of stabilizing cuff 14, thereby further reducing the amount of force required to advance catheter 10 within a body. More specifically, the pressure applied to stabilizing cuff 14 helps to flatten the stabilizing cuff's normally fluffy ingrowth fabric. Flattening or smoothing the ingrowth fabric of stabilizing cuff 14 in this manner may reduce the amount of drag created by the cuff, and may avoid the need for the application of conventional flattening adhesives which can be biodegradable; which, as explained above, may impede tissue ingrowth or result in a rigid, inflexible cuff structure.

Figure 8:
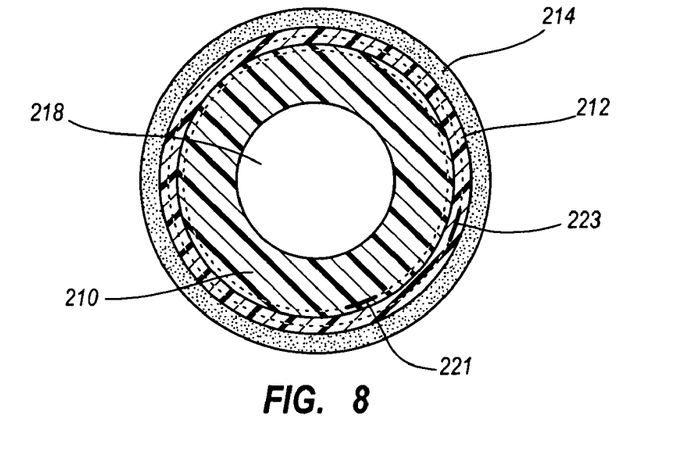
FIG. 8 is a cross-sectional view of an additional embodiment of a catheter assembly.

Moreover, the pressure and heat applied to stabilizing cuff 14 and tubular structure 12 in accordance with one or more of the exemplary embodiments described herein may also force at least a portion of stabilizing cuff 14 to become embedded in the tubular structure 12. Specifically, as tubular structure 12 begins to soften or melt upon application of sufficient heat, pressure applied by one or more of the apparatuses described herein may force at least a portion of the tubular structure 12 to flow into stabilizing cuff 14. For example, as illustrated in FIG. 8, a stabilizing cuff 214 may become at least partially embedded within the outer surface of tubular structure 212, as represented by depth of penetration line 223. As will be appreciated by one of ordinary skill in the art, at least partially embedding stabilizing cuff 214 within tubular structure 212 in this manner may strengthen the adhesion bond between stabilizing cuff 214 and tubular structure 212 to form a robust cuff structure. In addition, at least partially embedding stabilizing cuff 214 in this manner may reduce the outer diameter and profile of the cuff assembly, thereby reducing the amount of force required to advance catheter 210 within a body.

Similarly, in certain embodiments the pressure and heat applied to tubular structure 212 and catheter 210 may force at least a portion of tubular structure 212 to become embedded within the outer surface of catheter 210, as represented by depth of penetration line 221. In at least one embodiment, catheter 210 comprises a thermoplastic polyurethane resin that is substantially identical to a thermoplastic polyurethane resin utilized in tubular structure 212 to facilitate the embedding of tubular structure 212 within catheter 210. As with tubular structure 212 and stabilizing cuff 214, embedding tubular structure 212 within catheter 210 in this manner may strengthen the adhesion bond between tubular structure 212 and catheter 210, resulting in a robust cuff structure. In addition, at least partially embedding tubular structure 212 in this manner further may reduce the outer diameter and profile of the cuff assembly, thereby reducing the amount of force required to advance catheter 210 within a body.

Figure 5:
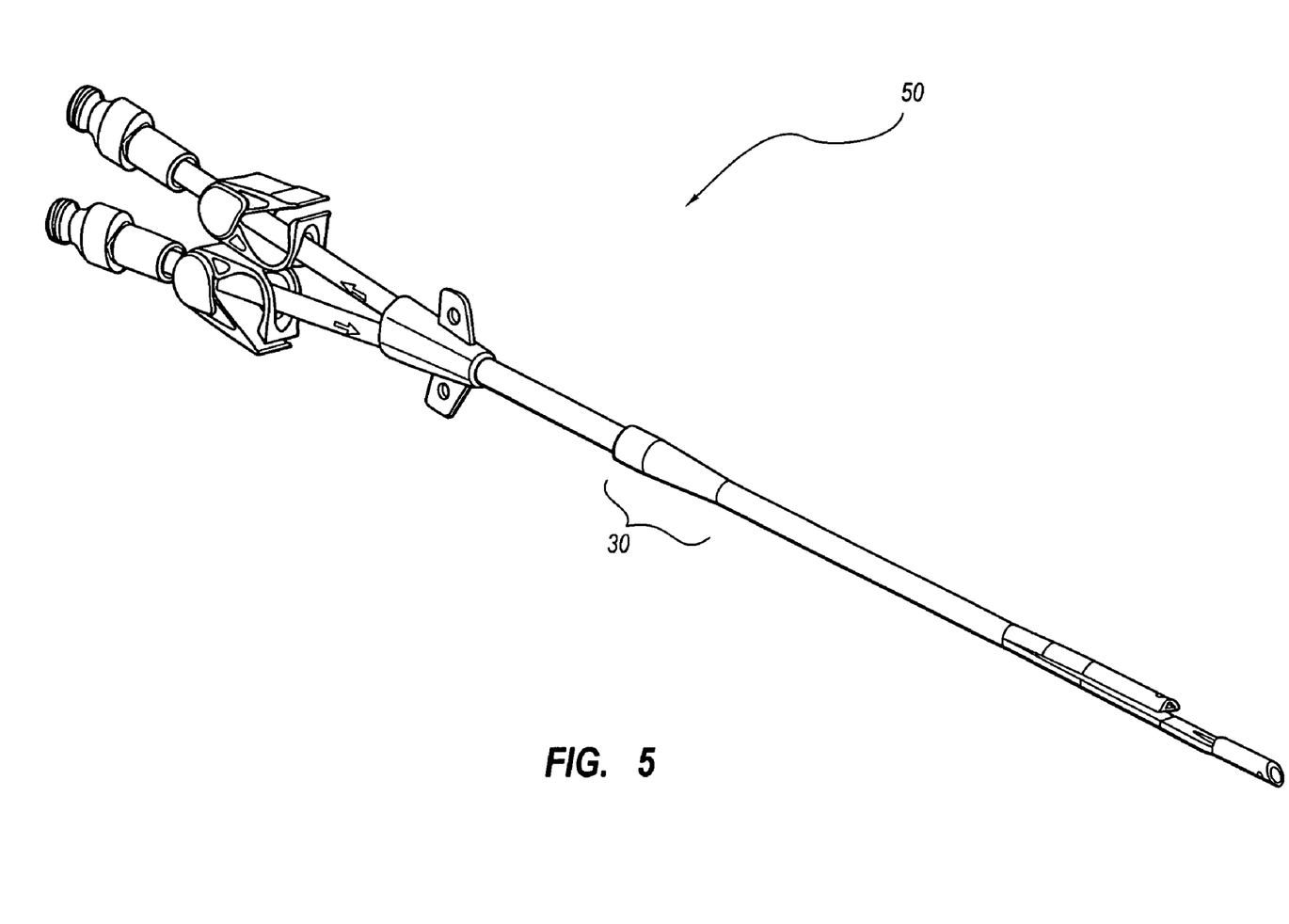
FIG. 5 is a perspective view of an exemplary catheter system comprising a catheter assembly according to at least one embodiment.

FIG. 5 is a perspective view of an exemplary catheter system 50 comprising a catheter assembly 30 according to certain embodiments. Catheter assembly 30 generally represents each catheter assembly described and/or illustrated herein, including the catheter assembly illustrated in FIG. 12. Generally speaking, catheter system 50 represents any system capable of introducing or removing fluid from a body, such as a human body. In any of the embodiments disclosed herein, the catheter can include one or more lumens. For example, catheter system 50 may represent a hemodialysis catheter system, an infusion catheter system, a cardiovascular access catheter system, a renal catheter system, a parenteral nutrition catheter system, a peritoneal dialysis catheter system, or any other catheter system without limitation.

Figure 9:
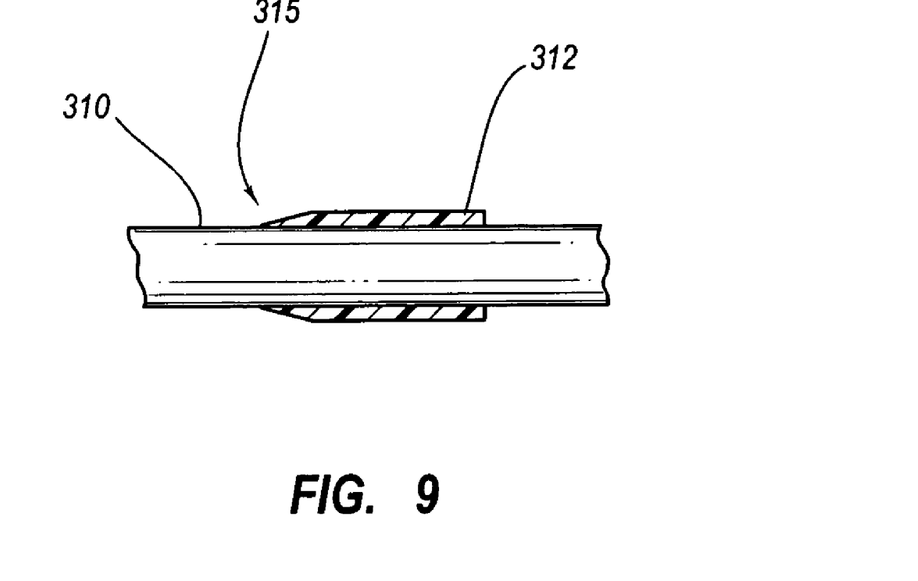
FIGS. 9-11 illustrate an additional exemplary method of manufacturing a catheter assembly.
Figure 10:
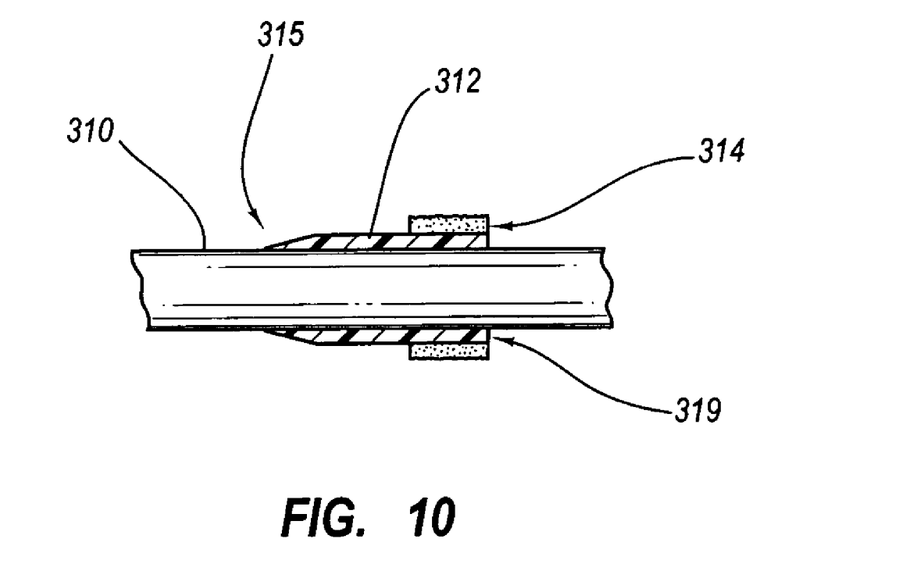
Figure 11:
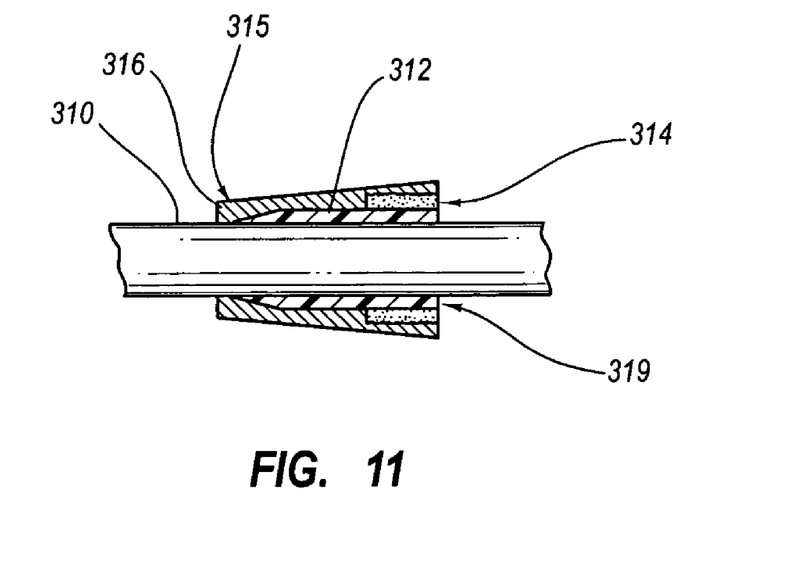

FIGS. 9-11 illustrate, in schematic cross-sectional views, an additional exemplary method of manufacturing a catheter assembly. Similar to FIGS. 1-3, these figures illustrate a tubular structure 312 slid over, or positioned generally about, the exterior surface of a catheter 310. However, in contrast to the tubular structure illustrated in FIGS. 1-3, tubular structure 312 may be preformed (i.e., shaped prior to positioning the tubular structure about the exterior surface of the catheter) to include at least one tapered end, such as the exemplary tapered surface extending generally from leading end 315 in FIGS. 9 and 10. More specifically, at least one end of tubular structure 312 may be preformed to taper down and away from an outer surface of stabilizing cuff 314 towards the outer diameter of catheter 310.

In at least one embodiment, the preformed tapered end is provided on an end of tubular structure 312 facing a direction of insertion, such as leading end 315 in FIGS. 9 and 10. Tubular structure 312 may also, however, be preformed such that both of its ends taper towards the outer surface of catheter 310. As illustrated in FIGS. 9-11, after preformed tubular structure 312 is positioned about catheter 310, a stabilizing cuff 314 may be affixed to tubular structure 312 and tubular structure 312 may be molded into a desired shape, in accordance with one or more of the embodiments discussed or illustrated herein. In at least one embodiment, catheter assembly 30 illustrated in FIG. 4 results from this process.

Preforming one or more of the ends of tubular structure 312 to include a tapered surface in this manner may reduce the amount of heat and pressure required to form the resulting catheter assembly. Specifically, the tapered shape of the ends of preformed tubular structure 312 may reduce the distance portions of tubular structure 312 must travel to form the desired shape illustrated in FIG. 4. Preformed tubular structure 312 may also reduce the amount of time required to mold tubular structure 312 into the desired shape, resulting in greater manufacturing efficiencies. In addition, preformed tubular structure 312 may help increase the yield of the manufacturing process.

Figure 12:
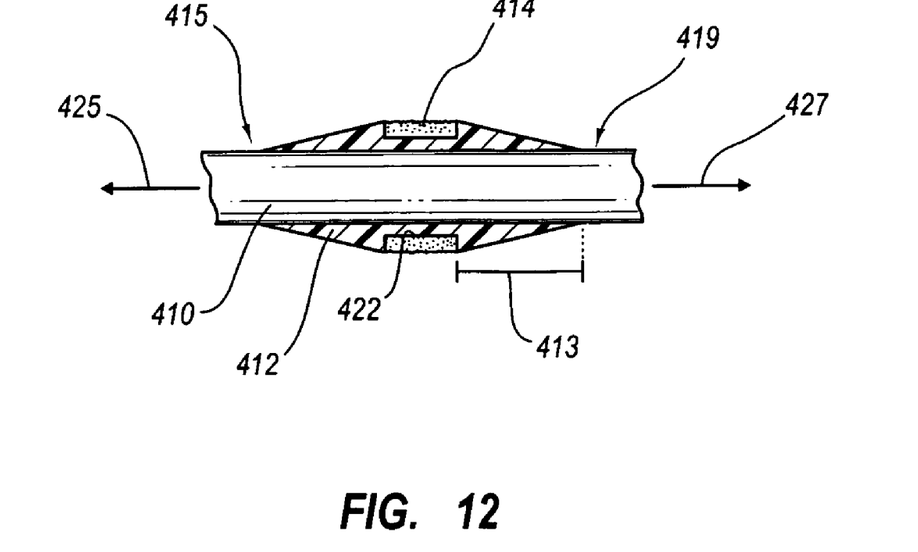
FIG. 12 is a partial schematic cross-sectional view of an additional embodiment of a catheter assembly.
Figure 13:
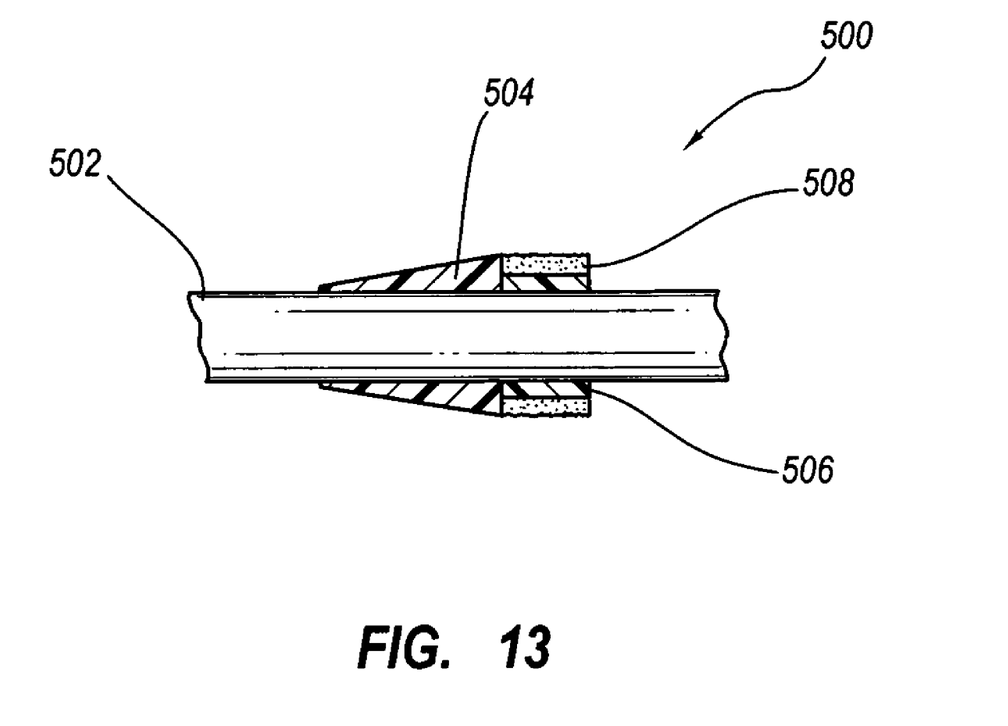
FIG. 13 is a partial schematic cross-sectional view of a further embodiment of a catheter assembly.

The preceding description has been provided to enable others skilled in the art to best utilize various aspects of the exemplary embodiments described herein. This exemplary description is not intended to be exhaustive or to be limited to any precise form disclosed. Many modifications and variations are possible without departing from the spirit and scope of the instant disclosure. For example, as illustrated in FIG. 12, a catheter assembly may be formed to facilitate advancement of a stabilizing cuff 414 within a body in either an antegrade direction 425 or a retrograde direction 427. Specifically, ends 415 and 419 of tubular structure 412 may be molded into the tapered shape illustrated in FIG. 12, resulting in a smooth and tapered transition from the outer diameter of a catheter 410 to stabilizing cuff 414 on either side of stabilizing cuff 414. Similarly, tubular structure 12 in FIG. 4 may shaped to include a tapered surface on either side of stabilizing cuff 14, as required.

In addition, the length of the tapered surfaces provided in the catheter assemblies illustrated in FIGS. 4 and 12, represented by element numbers 13 and 413, respectively, may be modified or adjusted as necessary. For example, a longer, more gradual taper may be provided to further reduce the transition angle between the outer surface of catheters 10, 410 and stabilizing cuffs 14, 414, respectively. Similarly, a shorter, steeper taper may be provided in order to reduce the amount of time and heat required to form the tapered shape and to control the quality and finish of the tapered surface. In at least one embodiment, the lengths 13 and 413 of the catheter assemblies rated in FIGS. 4 and 12 are equal to about 1 to 3 centimeters.

In another embodiment, a catheter assembly 500 includes a catheter body 502, a tapered member 504, a tubular member 506, and a stabilizing cuff 508 that can be at least partially embedded or affixed to the tubular 506. In particular embodiments, the tapered member 504 can be spaced away from the tubular member 506.

For ease of use, the words "including" and "having," as used in the specification and claims, are interchangeable with and have the same meaning as the word "comprising." It is intended that the scope of the instant disclosure be defined by the following claims.

What is claimed is:

1. A catheter assembly, comprising:
    a catheter including an inner surface defining one or more lumens therein;
    a tubular structure affixed to an exterior surface of the catheter;
    a stabilizing cuff affixed to the tubular structure;
    the tubular structure including only one tapered surface extending from an end of the tubular structure to the exterior surface of the catheter; and
    the stabilizing cuff being at least partially embedded within the tubular structure by the application of sufficient heat and pressure to cause at least a portion of the tubular structure to flow into the stabilizing cuff.

2. The catheter assembly of claim 1, wherein:
    the tubular structure further comprises an annular recess; and
    the stabilizing cuff is positioned substantially within the annular recess.

3. The catheter assembly of claim 1, wherein an exterior surface of the tubular structure is at least partially conical in shape.

4. The catheter assembly of claim 1, wherein an inner diameter of the tubular structure is configured to initially snugly fit around the exterior surface of the catheter.

5. The catheter assembly of claim 1, wherein the tapered surface of the tubular structure is configured to include a length of between about 1 to about 3 centimeters.

6. The catheter assembly of claim 1, wherein the tubular structure comprises at least one thermoplastic polyurethane resin.

7. The catheter assembly of claim 6, wherein the catheter comprises at least one thermoplastic polyurethane resin that is identical to a thermoplastic polyurethane resin that forms the tubular structure.

8. The catheter assembly of claim 3, wherein the at least one thermoplastic polyurethane resin is at least one of an aliphatic polyether-based polyurethane, an aromatic polyether-based polyurethane, and/or an aliphatic polycarbonate-based polyurethane.

9. A method of manufacturing a catheter assembly, comprising:
    providing a catheter;

positioning a tubular structure about the catheter;

positioning a stabilizing cuff near the tubular structure;

shaping the tubular structure to form only one tapered surface extending from an end of the tubular structure to an exterior surface of the catheter;

affixing the stabilizing cuff to the tubular structure; and embedding at least a portion of the stabilizing cuff within the tubular structure by the application of sufficient heat and pressure to cause at least a portion of the tubular structure to flow into the stabilizing cuff.

10. The method of claim 9, wherein shaping the tubular structure further comprises exceeding a glass transition temperature of the tubular structure.

11. The method of claim 9, wherein affixing the stabilizing cuff to the tubular structure comprises biasing the stabilizing cuff toward the catheter while exceeding a glass transition temperature of the tubular structure.

12. The method of claim 9, further comprising positioning a temporary sleeve about the tubular structure prior to shaping the tubular structure.

13. The method of claim 9, further comprising preforming the tubular structure to include at least one tapered end prior to positioning the tubular structure about the catheter.

14. The method of claim 9, further comprising applying an adhesion-resistant coating to the tubular structure prior to shaping the tubular structure.

* * * * *